United States Patent [19]
Teach

[11] 3,981,716
[45] Sept. 21, 1976

[54] GEM-BIS AMIDE HERBICIDE ANTIDOTE COMPOSITIONS AND METHODS OF USE

[75] Inventor: Eugene G. Teach, El Cerrito, Calif.

[73] Assignee: Stauffer Chemical Company, Westport, Conn.

[22] Filed: May 22, 1975

[21] Appl. No.: 580,125

Related U.S. Application Data

[62] Division of Ser. No. 363,464, May 24, 1973, Pat. No. 3,923,494.

[52] U.S. Cl. ............................. 71/100; 71/118
[51] Int. Cl.² ....................................... A01N 9/12
[58] Field of Search ............ 71/100, 118; 260/562 B

[56] References Cited
UNITED STATES PATENTS

| | | | |
|---|---|---|---|
| 2,743,247 | 4/1956 | Lotz | 260/562 B |
| 3,131,509 | 5/1964 | Hoffmann | 71/111 |
| 3,455,982 | 7/1969 | Watanabe et al. | 260/562 B |
| 3,564,768 | 2/1971 | Hoffmann | 71/100 |
| 3,719,466 | 3/1973 | Ahle | 71/118 |
| 3,867,444 | 2/1975 | Baker | 71/118 |

*Primary Examiner*—Glennon H. Hollrah
*Attorney, Agent, or Firm*—Harry A. Pacini

[57] ABSTRACT

Herbicidal compositions comprising an active herbicidal compound and antidote therefor and methods of use; the antidote compound corresponds to substituted gem-bis amides having the formula

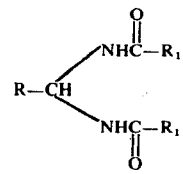

in which R is selected from the group alkyl, alkenyl, phenyl, phenalkyl, naphthyl, cyanoalkyl, and substituted phenyl wherein said substituents are selected from the group methoxy, nitro, chloro, bromo-3,4-methylenedioxy, mono- and di-substituted lower alkyl; and $R_1$ is lower haloalkyl.

28 Claims, No Drawings

GEM-BIS AMIDE HERBICIDE ANTIDOTE COMPOSITIONS AND METHODS OF USE

This is a division of application Ser. No. 363,464 filed May 24, 1973, now U.S. Pat. No. 3,923,494.

Background of the Invention

Among the many herbicidal compounds commercially available, the thiocarbamates alone or admixed with other herbicides, such as the triazines, have reached a relatively high degree of commercial success. These herbicides are immediately toxic to a large number of weed pests at different concentrations varying with the resistance of the weed pests. Some examples of these compounds are described and claimed in the U.S. Pat. Nos. 2,913,327, 3,037,853, 3,175,897, 3,185,720, 3,198,786 and 3,582,314. It has been found in practice that the use of these thiocarbamates as herbicides on crops sometimes causes serious injuries to the crop plant. When used in the recommended amounts in the soil to control many broadleaf weeds and grasses, serious malformation and stunting of the crop plants result. This abnormal growth in the crop plants results in loss of crop yield. Previous attempts to overcome this problem involves the treatment of the crop seed with certain antagonistic agents prior to plants, see U.S. Pat. Nos. 3,131,509 and 3,564,768. These antagonistic agents have not been notably successful. The aforementioned patent specifically exemplifies the treatment of seeds employing compounds of a different chemical class not suggestive of the present invention.

DESCRIPTION OF THE INVENTION

It has been discovered that plants can be protected against injury by the thiocarbamate-type herbicides, alone or mixed with other compounds and/or the tolerance of the plants can be substantially increased to the active compounds of the above-noted U.S. Patents by adding to the soil an antidote compound corresponding to the following formula:

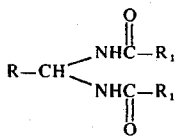

in which R is selected from the group alkyl, alkenyl, phenyl, phenalkenyl, naphthyl, cyanoalkyl and substituted phenyl wherein said substituents are selected from the group methoxy, nitro, chloro, bromo, 3,4-methylenedioxy, mono- and di-substituted lower alkyl; and $R_1$ is lower haloalkyl.

In the above description, the following embodiments are intended for the various substituent groups: For $R_1$, lower haloalkyl preferably includes, unless otherwise provided, those members which contain from 1 to 4 carbon atoms, inclusive, in both straight chain and branched chain configurations and the term halo includes chloro and bromo as mono-, di-, tri-, tetra- and per- substitutions, more preferably, mono-chloromethyl and dichloromethyl. For R, alkyl preferably includes those members containing from 1 to 6 carbon atoms, inclusive, in both branched and straight chain configuration; alkenyl preferably includes those members containing at least one olefinic double bond and from 2 to 6 carbon atoms, inclusive, in both branched and straight chain configurations; the term phenalkenyl preferably includes phenyl substituted alkenyl in which the alkenyl contains at least one unsaturated double bond and from 2 to 4 carbon atoms, in both straight chain and branched chain configurations, for example, styryl, 1-methylstyryl and the like; the term cyanoalkyl preferably includes those members which contain from 2 to 6 carbon atoms, inclusive; for R, phenyl substituted wherein the substituents are mono- and disubstituted lower alkyl is meant tolyl and xylyl, i.e., monomethylphenyl and dimethylphenyl substitution and also includes other lower alkyl moieties having from 1 to 4 carbon atoms, inclusive, in branched chain and straight chain configurations.

As an alternative mode of action, the compounds of this invention may interfere with the normal herbicidal action of the thiocarbamate-type and other herbicides to render them selective in their action. Whichever mode of action is present, the corresponding beneficial and desirable effect is the continued herbicidal effect of the thiocarbamate with the accompanying decreased herbicidal effect on desired crop species. This advantage and utility will become more apparent hereinafter.

Therefore, the terms herbicide, antidote or antidotal amount, is meant to describe that effect which tends to counteract the normal injurious herbicidal response that the herbicide might otherwise produce. Whether it is to be termed a remedy, interferant, protectant, or the like, will depend upon the exact mode of action. The mode of action is varied, but the effect, which is desirable, is the result of the method of treating the soil in which a crop is planted. Hitherto, there have been no systems which have been satisfactory for this purpose.

The compounds of this invention represented by the above formula can be prepared by several different procedures depending upon the starting materials.

The gem-bis-amides of this invention can be prepared by combining an aldehyde with an amide and an acid catalyst, such as p-toluene sulfonic acid, in a solvent, such as benzene or toluene. The reaction mixture is heated at reflux until the theoretical amount of water is removed with a Dean-Start apparatus. Most of the products were solids which crystallized out of the solvent on cooling, therefore, after the reaction is complete, the end product is readily recovered by normal work-up procedures.

The compounds of the present invention and their preparation are more particularly illustrated by the following examples. Following the examples of preparation is a table of compounds which are prepared according to the procedures described herein. Compound numbers have been assigned to them and are used for identification throughout the balance of the specification.

EXAMPLE I

Preparation of α, α-bis-dichloroacetamido-4'-nitro toluene.

Dichloroacetamide, 6.4 g., p-nitrobenzaldehyde, 3.8 g., and p-toluene sulfonic acid, 0.1 g. are combined in 100 ml. of toluene and heated at reflux until 0.5 ml. of water is removed in a Dean-Start apparatus. The product, which crystallizes from the toluene solution, weighs 7.6 g. and melts at 224°–227°C. with decomposition.

EXAMPLE II

Preparation of 1,1-bis-dichloroacetamido-3-phenyl-3-propene.

Cinnamaldehyde, 2.6 g., dichloroacetamide, 5.1 g., and p-toluene sulfonic acid, 0.1 g., are heated to reflux in 100 ml. of toluene under a Dean-Start apparatus until 0.4 ml. of water is removed. The product is recovered by filtration. A sample of the title compound triturated with ether had a melting point of 168°–170°C. with decomposition.

EXAMPLE III

Preparation of α, α-bis-dichloroacetamido butane.

Butyraldehyde, 2.2 g., dichloroacetamide, 7.7 g., and p-toluene sulfonic acid, 0.5 g. are combined in 100 ml. of benzene and heated to reflux under a Dean-Start apparatus. After 1 hour, 0.5 ml. of water is removed and the mixture is cooled and the product recovered by filtration. The yield of title compound is 2.6 g., m.p. 165°–168°C. Additional product is recovered by removing the benzene under vacuum.

EXAMPLE IV

Preparation of α, α-bis-chloroacetamido toluene.

Benzaldehyde, 4.2 g., is combined with 7.5 g. of chloroacetamide and 0.5 g. of p-toluene sulfonic acid in 100 ml. of toluene. The mixture is heated at reflux under a Dean-Stark apparatus until 0.75 ml. of water has been removed. The product which crystallized out on cooling weighed 10.1 g. and melted at 192°–195°C.

EXAMPLE V

Preparation of 1,1-bis-dichloroacetamido-2,2-dimethyl-4-cyano butane.

Ibanitrile, 3.1 g., dichloroacetamide, 6.4 g., and 0.1 g. p-toluene sulfonic acid are combined in 100 ml. of toluene and heated at reflux under a Dean-Stark apparatus until 0.5 ml. of water is recovered. The product which is soluble in toluene was obtained by removing the toluene under vacuum. There is obtained 4.4 g. of the title compound, an oil, $N_D^{30}$ 1.4650.

TABLE I $$R-CH\begin{matrix}NHC(=O)-R_1\\NHC(=O)-R_1\end{matrix}$$

| COMPOUND NUMBER | R | $R_1$ | m.p. °C. or $N_D^{30}$ |
|---|---|---|---|
| 1 | p-Br-phenyl | $CHCl_2$ | 218–221 |
| 2 | 3,4-methylenedioxyphenyl | $CHCl_2$ | 195–198 |
| 3 | p-$NO_2$-phenyl | $CHCl_2$ | 224–227 |
| 4 | 2,4-di-$NO_2$-phenyl | $CHCl_2$ | 159 |
| 5 | 3,4-$CH_3O$-phenyl | $CHCl_2$ | 200–203 |
| 6 | $C_6H_5(CH=CH-)$ | $CHCl_2$ | 168–170 |
| 7 | $C_6H_5(CH=C(CH_3)-)$ | $CHCl_2$ | 188–193 |
| 8 | 2,4-$Cl_2$-phenyl | $CHCl_2$ | 233–234 |
| 9 | o-$CH_3$-phenyl | $CHCl_2$ | 218–212 |
| 10 | m-$CH_3$-phenyl | $CHCl_2$ | 211–212 |
| 11 | p-$CH_3$-phenyl | $CHCl_2$ | 220–223 |
| 12 | o-Cl-phenyl | $CHCl_2$ | 224–225 |
| 13 | m-Cl-phenyl | $CHCl_2$ | 211–212 |
| 14 | p-Cl-phenyl | $CHCl_2$ | 236–237 |
| 15 | o-$CH_3O$-phenyl | $CHCl_2$ | 208–209 |
| 16 | m-$CH_3O$-phenyl | $CHCl_2$ | 197–199 |
| 17 | 1-naphthyl | $CHCl_2$ | 211–213 |
| 18 | p-i-$C_3H_7$-phenyl | $CHCl_2$ | 210–211 |
| 19 | 2,5-$CH_3O$-phenyl | $CHCl_2$ | 201–202 |
| 20 | 3,4-$CH_3O$-phenyl | $CHCl_2$ | 192–195 |
| 21 | n-$C_3H_7$ | $CHCl_2$ | 165–168 |
| 22 | n-$C_3H_7$ | $CH_2Cl$ | 162–163 |
| 23 | i-$C_3H_7$ | $CH_2Cl$ | 185–186 |
| 24 | $C_6H_5$ | $CHCl_2$ | 214 |
| 25 | m-$NO_2$-phenyl | $CHCl_2$ | 149 |
| 26 | $CH_2=CH$ | $CHCl_2$ | 142–150 |
| 27 | $C_6H_5$ | $CH_2Cl$ | 192–195 |
| 28 | m-$NO_2$-phenyl | $CH_2Cl$ | 197–199 |
| 29 | 2,6-$Cl_2$-phenyl | $CHCl_2$ | 199–201 |
| 30 | $N\equiv C-CH_2CH_2C(CH_3)_2-$ | $CHCl_2$ | 1.4650 |

The compounds of this invention were employed in effective herbicidal antidote compositions comprising thiocarbamates in combination with antidote compounds described hereinabove. They were tested in the following manner.

Procedure: Multicrop Antidote Screen

Plastic flats were filled with Felton loamy sand soil. Since a variety of grass and broadleaf crops were used in these tests, EPTAM (EPTC) was incorporated at 1/2 and 5 lb/A., while a constant rate of 5 lb/A. of the additive was used. LASSO (2-chloro-2',6'-diethyl-N-(methoxymethyl)acetanilide. EPTAM (EPTC) and the herbicide antidote were applied separately by pipetting measured amounts of the appropriate stock solutions into the soil during incorporation in a 5 gallon rotary cement mixer. Stock solutions were prepared as follows:

A. 1/2 lb/A.: 670 mg. of EPTC 6E (75.5% a.i.) is diluted with 500 ml. of deionized water so that 2 ml. equals 1/2 lb/A. flat.

B. 5 lb/A.: 6700 mg. of EPTC 6E (75.5%) is diluted with 500 ml. of deionized water so that 2 ml. equals 5 lb/A. flat.

C. 2 lb/A.: 427 mg. LASSO 4E is diluted with 100 ml. of deionized water so that 1 ml. equals 2.05 mg. (a.i.) and 4 ml. equals 8.2 mg. equivalent to 2 lb/A. flat.

Antidote stock solutions are prepared by diluting 102 mg. of technical material with 10 ml. of acetone 1% Tween 20 (polyoxyethylene sorbitan monolaurate) so that 2 ml. equals 5 lb/A. flat.

After the soil is treated with both herbicide and additive, the soil is transferred from the mixer back into the flat where it is then prepared for seeding. The initial step in preparation is to remove a one pint sample of soil from each flat to be retained and used to cover the seeds after planting. The soil is then leveled and rows one-quarter inch deep are made in each flat. Flats treated with 5 lb/A. of EPTAM are seeded to DeKalb XL-44 corn (*Zea maize*), US H9 sugarbeets (*Beta vulgare*), small seeded gray striped sunflower (Helianthus annus), Acala cotton (*Gossypium hirsutum*), Brag soybeans (*Glycine max*) and oilseed rape (*Brassica Napus*). Flats treated with 1/2 lb/A. of EPTAM are seeded to red oats (*Avena byzantina*), R-10 milo (*Sorghum vulgare*), Fremont HRS wheat (*Triticum aestivum*), giant foxtail (*Seteria feberii*), Calrose rice (*Oryza sativa*) and Blue Mariate barley (*Hordeum vulgare*). Flats treated with 2 lb/A. of LASSO are seeded to DeKalb XL-44 corn (*Zea maize*), Fremont HRS wheat (*Triticum aestivum*), Calrose rice (*Oryza sativa*), R-10 milo (*Sorghum vulgare*), and Numar barley (*Hordeum vulgare*). Seeds are then covered with the pint soil sample removed prior to seeding.

The flats are then placed on greenhouse benches where temperatures are maintained between 70°–90°F. The soil is watered by sprinkling to assure good plant growth.

Injury ratings are taken 2 and 4 weeks after the treatments are applied. Soil treated with the herbicides alone at 1/2, 2 or 5 lb/A. is included to provide a basis for determining the amount of injury reduction provided by the herbicide antidotes. The per cent protection is determined by a comparision with flats not treated with the candidate antidote.

TABLE II

| COMPOUND NUMBER | Multicrop Screen Results Percent Protection | | |
|---|---|---|---|
| | Rate of Herbicide lb/A. | Crop | % Protection (4 weeks) |
| 1 | LASSO** 2.0 | wheat | 40[a] |
| | LASSO 2.0 | milo | 37[a] |
| | EPTC* 5.0 | corn | 100 |
| 2 | EPTC 0.5 | wheat | 100 |
| | LASSO 2.0 | milo | 37[a] |
| | EPTC 0.5 | barley | 100 |
| | EPTC 5.0 | corn | 100 |
| 3 | EPTC 0.5 | milo | 67 |
| | LASSO 2.0 | milo | 26[a] |
| 4 | LASSO 2.0 | wheat | 18[a] |
| 5 | EPTC 5.0 | corn | 90 |
| 6 | LASSO 2.0 | wheat | 30[a] |
| | EPTC 0.5 | barley | 80 |
| | EPTC 5.0 | corn | 100 |
| 7 | EPTC 5.0 | corn | 70 |
| 8 | EPTC 5.0 | corn | 100 |
| 9 | EPTC 5.0 | corn | 100 |
| 10 | EPTC 5.0 | corn | 100 |
| 11 | LASSO 2.0 | milo | 15[a] |
| | LASSO 2.0 | wheat | 40[a] |
| | EPTC 5.0 | corn | 100 |
| 12 | EPTC 5.0 | corn | 100 |
| 13 | LASSO 2.0 | wheat | 50[a] |
| | LASSO 2.0 | milo | 47[a] |
| | EPTC 0.5 | barley | 75 |
| | EPTC 5.0 | corn | 100 |
| 14 | EPTC 0.5 | milo | 40 |
| | EPTC 0.5 | wheat | 20 |
| | EPTC 0.5 | barley | 100 |
| | EPTC 5.0 | corn | 100 |
| 15 | EPTC 5.0 | corn | 100 |
| 16 | EPTC 5.0 | corn | 100 |
| 17 | EPTC 5.0 | corn | 100 |
| 18 | EPTC 5.0 | corn | 100 |
| 19 | EPTC 5.0 | corn | 100 |
| 20 | EPTC 5.0 | corn | 100 |
| 21 | EPTC 0.5 | wheat | 20 |
| | EPTC 5.0 | corn | 100 |
| 22 | EPTC 0.5 | milo | 22 |
| | EPTC 5.0 | corn | 23 |
| 23 | LASSO 2.0 | wheat | 40[a] |
| | LASSO 2.0 | milo | 26[a] |
| | EPTC 0.5 | milo | 22 |
| | EPTC 0.5 | wheat | 20 |
| | EPTC 5.0 | corn | 22 |
| 30 | LASSO 2.0 | wheat | 30[a] |

*S-ethyl dipropylthiocarbamate
**2-chloro-2′,6′-diethyl-N-(methoxymethyl) acetanilide
[a]2 weeks

Corn Seed Treatment Test

Small flats were filled with Felton loamy sand soil. Soil incorporated herbicides were applied at this time. The soil from each flat was placed into a five-gallon cement mixer where the soil was mixed as the herbicides were applied using a predetermined amount of a stock solution containing 936 mg. of 75.5% active ingredient to 100 ml. of water. One ml. of stock solution was applied to the soil in a volumetric pipet for each pound of herbicide desired. One ml. of stock solution contained 7 mg. of herbicide which equals one pound per acre when applied to the soil in the flats. After the herbicide incorporation, the soil was placed back into the flats.

Flats of herbicide-treated and untreated soil were then ready to be planted. A pint sample of soil was removed from each flat and placed next to each flat for later use in covering up the seeds. The soil was leveled and rows one-half inch deep were made for planting seeds. Alternating rows of treated and untreated crop seeds were sown. In each test, six PAG 344T field corn seeds were planted in each row. Rows were approximately 1½ inches apart in the flat. Seeds were treated by placing 50 mg. of the antidote compound with 10 grams of corn seed (0.5% w/w) in a suitable container and shaking them until the seeds were uniformly covered with the compound. Antidote compounds were also applied as liquid slurries and powders or dusts. In some cases, acetone was used to dissolve powdered or solid compounds so they could be more effectively applied to the seeds.

After the flats were seeded, they were covered with the one pint of soil which had been removed just prior to planting. Flats were placed on greenhouse benches where temperatures ranged from 70°–90°F. Flats were watered by sprinkling as needed to assure good plant growth. Per cent control ratings were taken 2, 3 and 4 weeks after the treatments were applied.

In each test, the herbicide was applied alone, in combination with the seed protectant, and the seed protectant was applied alone to check for phytotoxicity. The degree of the protective effect was noted by comparison with the control. The results of these tests are tabulated in Table III.

TABLE III

| Percent Injury to Corn from EPTC* (6 lb/A.) Seed Treatment Test | |
|---|---|
| | Percent Protection, 2 weeks Treated |
| COMPOUND NUMBER | Seed (0.5% w/w) |
| 24 | 75% |
| 25 | 62.5% |
| 26 | 37.5% |
| 27 | 75% |
| 28 | 25% |
| 29 | 75% |

*S-ethyl dipropylthiocarbamate

The antidote compounds and compositions of the present invention can be used in any convenient form. Thus, the antidote compounds can be formulated into emulsifiable liquids, emulsifiable concentrates, liquid, wettable powder, powders, granular or any other convenient form. In its preferred form, a nonphytotoxic quantity of an herbicidal antidote compound is admixed with a selected herbicide and incorporated into the soil prior to or after planting the seed. It is to be understood, however, that the herbicides can be incorporated into the soil and thereafter the antidote compound can be incorporated into the soil. Moreover, the crop seed itself can be treated with a non-phytotoxic quantity of the compound and planted into the soil which has been treated with herbicides, or untreated with the herbicide and subsequently treated with the herbicide. The addition of the antidote compound does not affect the herbicidal activity of the herbicides.

The amount of antidote compound present can range between about 0.01 to about 15 parts by weight of antidote compound described herein per each part by weight of herbicide. The exact amount of antidote compound will usually be determined on economic ratios for the most effective amount usable. It is understood that a non-phytotoxic quantity of antidote compound will be employed in the herbicidal compositions described herein.

The herbicides indicated in the tables and elsewhere are used at rates which produce effective control of undesirable vegetation. The rates are within the recommended amounts set forth by the supplier. Therefore, the weed control in each instance is commercially acceptable within the desired or recommended amount.

It is clear that the classes of herbicidal agents described and illustrated herein are characterized as effective herbicides exhibiting such activity. The degree of this herbicidal activity varies among specific compounds and among combinations of specific compounds within the classes. Similarly, the degree of activity to some extent varies among the species of plants to which a specific herbicidal compound or combination may be applied. Thus, selection of a specific herbicidal compound or combination to control undesirable plant species readily may be made. Within the present invention are prevention of injury to a desired crop species in the presence of a specific compound or combination may be achieved. The beneficial plant species which can be protected by this method is not intended to be limited by the specific crops employed in the examples.

The herbicidal compounds employed in the utility of this invention are active herbicides of a general type. That is, the members of the classes are herbicidally effective against a wide range of plant species with no discrimination between desirable and undesirable species. The method of controlling vegetation comprises applying an herbicidally effective amount of the herein-described herbicidal compounds to the area or plant locus where control is desired. The compositions as set forth in this invention include those wherein the preferred active herbicidal compound is selected from EPTC, S-ethyl diisobutyl thiocarbamate, S-propyl dipropyl thiocarbamate, S-2,3,3-trichloroallyl-diisopropyl thiocarbamate, S-ethyl cyclohexyl ethyl thiocarbamate, 2-chloro-2',6'-diethyl-N-(methoxymethyl)acetanilide, S-ethyl hexahydro-1H-azepine-1-carbothioate, 2-chloro-N-isopropylacetanilide, N,N-diallyl-2-chloroacetamide, S-4-chlorobenzyl diethyl thiocarbamate, 2-chloro-4-ethylamino-6-isopropylaminos-triazine, 2-chloro-4,6-bis(ethylamino)-s-triazine, 2(4-chloro6-ethylamine-s-triazine-2-yl-amino)-2-methyl-propionitrile, 2-chloro-4-cyclopropylamino-6-isopropylamino-s-triazine, 2,4-dichlorophenoxyacetic acid, its esters and salts, and 3-)3,4-dichlorophenoxyacetic acid, its esters and salts, and 3-(3,4-dichlorophenyl)-1,1-dimethylurea and combination thereof.

An herbicide as used herein means a compound which controls or modifies the growth of vegetation or plants. Such controlling or modifying effects include all deviations from natural development; for example, killing, retardation, defoliation, desiccation, regulation, stunting, tillering, stimulation, dwarfing and the like.

By "plants", it is meant germinant seeds, emerging seedlings, and established vegetation, including the roots and above-ground portions.

What is claimed is:

1. An herbicide composition comprising a mixture of a herbicidally effective amount of a thiocarbamate herbicide and an antidote compound corresponding to the formula

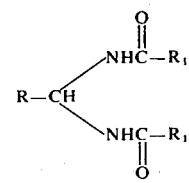

in which R is selected from the group phenyl, naphthyl and substituted phenyl wherein said substituents are selected from the group methoxy, nitro, chloro, bromo, mono- and di-substituted lower alkyl having from 1 to 4 carbon atoms, inclusive; and $R_1$ is lower chloroalkyl containing from 1 to 4 carbon atoms, inclusive; from about 0.01 to about 15 parts by weight of antidote compound for each part by weight of the thiocarbamate herbicide.

2. The composition according to claim 1 in which R is halophenyl.
3. The composition according to claim 2 in which R is p-bromophenyl and $R_1$ is dichloromethyl.
4. The composition according to claim 2 in which R is 2,6-dichlorophenyl and $R_1$ is dichloromethyl.
5. The composition according to claim 2 in which R is o-chlorophenyl and $R_1$ is dichloromethyl.
6. The composition according to claim 2 in which R is m-chlorophenyl and $R_1$ is dichloromethyl.
7. The composition according to claim 2 in which R is p-chlorophenyl and $R_1$ is dichloromethyl.
8. The composition according to claim 2 in which R is 2,4-dichlorophenyl and $R_1$ is dichloromethyl.
9. The composition according to claim 1 in which R is lower alkyl substituted phenyl.
10. The composition according to claim 9 in which R is o-methylphenyl and $R_1$ is dichloromethyl.
11. The composition according to claim 9 in which R is m-methylphenyl and $R_1$ is dichloromethyl.
12. The composition according to claim 9 in which R is p-methylphenyl and $R_1$ is dichloromethyl.
13. The composition according to claim 9 in which R is p-isopropylphenyl and $R_1$ is dichloromethyl.
14. The composition according to claim 1 in which R is methoxy substituted phenyl.
15. The composition according to claim 14 in which R is 3,4-dimethoxyphenyl and $R_1$ is dichloromethyl.
16. The composition according to claim 14 in which R is o-methoxyphenyl and $R_1$ is dichloromethyl.
17. The composition according to claim 14 in which R is m-methoxyphenyl and $R_1$ is dichloromethyl.
18. The composition according to claim 14 in which R is 2,5-dimethoxyphenyl and $R_1$ is dichloromethyl.
19. The composition according to claim 14 in which R is 3,4-dimethoxyphenyl and $R_1$ is dichloromethyl.
20. The composition according to claim 1 in which R is nitrophenyl.
21. The composition according to claim 20 in which R is p-nitrophenyl and $R_1$ is dichloromethyl.

22. The composition according to claim 20 in which R is m-nitrophenyl and $R_1$ is monochloromethyl.

23. The composition according to claim 20 in which R is m-nitrophenyl and $R_1$ is dichloromethyl.

24. The composition according to claim 1 in which R is naphthyl.

25. The composition according to claim 24 in which R is 1-naphthyl and $R_1$ is dichloromethyl.

26. In the method of controlling weeds wherein a thiocarbamate herbicide is applied to the habitat of said weeds, the improvement comprising applying to the habitat thereof from about 0.01 to about 15 parts by weight for each part by weight of the thiocarbamate herbicide an antidote compound corresponding to the formula

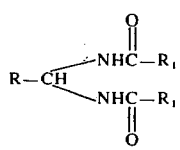

in which R is selected from the group phenyl, naphthyl, and substituted phenyl wherein said substituents are selected from the group methoxy, nitro, chloro, bromo, mono- and di-substituted lower alkyl having from 1 to 4 carbon atoms, inclusive; and $R_1$ is lower chloroalkyl containing from 1 to 4 carbon atoms, inclusive.

27. The method of protecting corn crop from injury due to a thiocarbamate herbicide, comprising applying to the corn seed prior to planting a non-phytotoxic antidotally effective amount of a compound corresponding to the formula

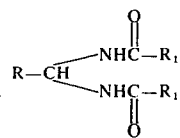

in which R is selected from the group phenyl, naphthyl, and substituted phenyl wherein said substituents are selected from the group methoxy, nitro, chloro, bromo, mono- and di-substituted lower alkyl having from 1 to 4 carbon atoms, inclusive; and $R_1$ is lower chloroalkyl containing from 1 to 4 carbon atoms, inclusive.

28. The method of protecting corn crop from injury due to a thiocarbamate herbicide, comprising preplant incorporation in the soil in which said corn crop is to be planted, from about 0.01 to about 15 parts by weight for each part by weight of the thiocarbamate herbicide, a non-phytotoxic antidotally effective amount of a compound corresponding to the formula

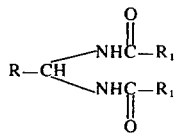

in which R is selected from the group phenyl, haphthyl, and substituted phenyl wherein said substituents are selected from the group methoxy, nitro, chloro, bromo, mono- and di-substituted lower alkyl having from 1 to 4 carbon atoms, inclusive; and $R_1$ is lower chloroalkyl containing from 1 to 4 carbon atoms, inclusive;

* * * * *

Disclaimer 3,981,716.—*Eugene G. Teach*, El Cerrito, Calif. GEM-BIS AMIDE HERBICIDE ANTIDOTE COMPOSITIONS AND METHODS OF USE. Patent dated Sept. 21, 1976. Disclaimer filed Nov. 21, 1977, by the assignee, *Stauffer Chemical Company*.

Hereby enters this disclaimer to claims 1 through 28 of said patent.

[*Official Gazette April 18, 1978.*]